(12) United States Patent
Wang et al.

(10) Patent No.: US 11,354,783 B2
(45) Date of Patent: *Jun. 7, 2022

(54) METHOD AND APPARATUS OF SHARPENING OF GASTROINTESTINAL IMAGES BASED ON DEPTH INFORMATION

(71) Applicant: CAPSO VISION, Inc., Saratoga, CA (US)

(72) Inventors: Kang-Huai Wang, Saratoga, CA (US); Gordon C Wilson, San Francisco, CA (US); Chenyu Wu, Sunnyvale, CA (US)

(73) Assignee: CapsoVision Inc., Saratoga, CA (US)

( * ) Notice: Subject to any disclaimer, the term of this patent is extended or adjusted under 35 U.S.C. 154(b) by 182 days.

This patent is subject to a terminal disclaimer.

(21) Appl. No.: 16/703,765

(22) Filed: Dec. 4, 2019

(65) Prior Publication Data

US 2020/0104983 A1 Apr. 2, 2020

Related U.S. Application Data

(63) Continuation-in-part of application No. 16/682,208, filed on Nov. 13, 2019, now Pat. No. 10,943,333, (Continued)

(51) Int. Cl.
*H04N 7/18* (2006.01)
*G06T 5/00* (2006.01)
(Continued)

(52) U.S. Cl.
CPC .............. *G06T 5/003* (2013.01); *A61B 1/041* (2013.01); *G06T 7/0012* (2013.01);
(Continued)

(58) Field of Classification Search
CPC .................. G06T 5/003; G06T 7/0012; G06T 2207/20182; G06T 2207/30092;
(Continued)

(56) References Cited

U.S. PATENT DOCUMENTS 7,627,193 B2 * 12/2009 Alon .................. G02B 27/0012
348/240.3
7,920,172 B2 4/2011 Chanas et al.
(Continued)

FOREIGN PATENT DOCUMENTS

WO WO 03/053241 A2 7/2003

*Primary Examiner* — Shan E Elahi
(74) *Attorney, Agent, or Firm* — Blairtech Solution LLC

(57) ABSTRACT

A method and apparatus for sharpening gastrointestinal (GI) images are disclosed. A target distance between the target region and the imaging apparatus is determined for a target region in the regular image. One or more filter parameters of a de-blurring filter are selected from stored filter parameters according to the target distance. A processed target region is generated by applying the de-blurring filter to the target region to improve sharpness of the target region. A method for characterizing an imaging apparatus is also disclosed. The imaging apparatus is placed under a controlled environment. Test pictures for one or more test patterns are captured at multiple test distances in a range including a focus distance using the imaging apparatus. One or more parameters associated a target point spread function are determined from each test picture for characterizing image formation of the imaging apparatus at the selected distance.

30 Claims, 6 Drawing Sheets

Related U.S. Application Data which is a continuation-in-part of application No. 16/543,922, filed on Aug. 19, 2019, now Pat. No. 10,624,533, which is a continuation-in-part of application No. 15/927,856, filed on Mar. 21, 2018, now Pat. No. 10,531,074, which is a continuation-in-part of application No. 14/884,788, filed on Oct. 16, 2015, now Pat. No. 9,936,151.

(51) Int. Cl.
*G06T 7/00* (2017.01)
*A61B 1/04* (2006.01)

(52) U.S. Cl.
CPC .............. *G06T 2207/20024* (2013.01); *G06T 2207/20182* (2013.01); *G06T 2207/30092* (2013.01)

(58) Field of Classification Search
CPC . G06T 2207/20024; G06T 2207/10068; A61B 1/041; A61B 1/00009
USPC ......................................................... 348/135
See application file for complete search history.

(56) References Cited

U.S. PATENT DOCUMENTS

| | | |
|---|---|---|
| 7,983,458 B2 | 7/2011 | Wang |
| 8,270,083 B2 | 9/2012 | Liege et al. |
| 10,785,428 B2* | 9/2020 | Wang ..................... A61B 1/06 |
| 10,943,333 B2* | 3/2021 | Wang ..................... A61B 1/273 |
| 2007/0098379 A1* | 5/2007 | Wang .................. H04N 19/172 396/14 |
| 2007/0115378 A1* | 5/2007 | Wang ..................... A61B 1/041 348/308 |
| 2007/0201130 A1* | 8/2007 | Fujinoki .............. A61B 5/0059 359/398 |
| 2008/0170124 A1* | 7/2008 | Hatanaka ........... H04N 5/23248 348/208.4 |
| 2009/0102763 A1* | 4/2009 | Border ................... H04N 7/144 345/87 |
| 2009/0284589 A1* | 11/2009 | Radeva ................ G06T 7/0012 348/77 |
| 2010/0272318 A1 | 10/2010 | Cabiri et al. |
| 2012/0035507 A1 | 2/2012 | George et al. |
| 2014/0221741 A1* | 8/2014 | Wang .................... A61B 5/073 600/109 |
| 2017/0046833 A1 | 2/2017 | Lurie et al. |
| 2019/0129026 A1* | 5/2019 | Sumi .................. G01S 7/52039 |

* cited by examiner

METHOD AND APPARATUS OF SHARPENING OF GASTROINTESTINAL IMAGES BASED ON DEPTH INFORMATION

CROSS REFERENCE TO RELATED APPLICATIONS

The present invention is continuation-in-part of and claims priority to U.S. application Ser. No. 16/682,208, filed on Nov. 13, 2019, which is continuation-in-part of and claims priority to U.S. application Ser. No. 16/543,922, filed on Aug. 19, 2019, which is continuation-in-part of and claims priority to U.S. application Ser. No. 15/927,856, filed on Mar. 21, 2018, which is continuation-in-part of and claims priority to U.S. application Ser. No. 14/884,788, filed on Oct. 16, 2015, now U.S. Pat. No. 9,936,151. The U.S. Patent Applications and U.S. Patent are hereby incorporated by reference in their entireties.

FIELD OF THE INVENTION

The present invention relates to in vivo capsule camera. In particular, the present invention discloses an endoscope capable of deriving depth map from structured-light images and techniques for optimizing regular image quality based on the derived depth map.

BACKGROUND AND RELATED ART

As is known in the field, capsule endoscopes can be used to image the mucosa of the entire gastrointestinal (GI) tract from the esophagus through the colon. Since the capsule position within the GI tract is not generally under a clinician's control, it must image both surfaces that are touching the capsule and mucosal surfaces that are several centimeters from the capsule (e.g. in large organs such as the colon and stomach). However, the camera depth of field (DOF) for the devices being used today is not large enough to produce an optimally sharp image over the required range of object distances. Furthermore, capsule endoscope cameras are always fixed focus. The constraints of size and power make variable focus implementation difficult. Even if variable focus capsule endoscopes may be deployed in the future, they cannot make the entire image sharp when close and near objects are in the same frame. Accordingly, it is desirable to develop a capsule endoscope that can always provide, or allows for deriving, high quality images for near as well as far objects in one same frame.

SUMMARY OF THE INVENTION

A method and apparatus for processing gastrointestinal (GI) images are disclosed. According to this method, a regular image is received, where the regular image is captured using an imaging apparatus by projecting non-structured light onto a body lumen when the imaging apparatus is in the body lumen. A target distance is determined for a target region in the regular image, where the target distance is between the target region and the imaging apparatus. One or more filter parameters of a de-blurring filter are determined from stored test pictures or from stored filter parameters according to the target distance. A first processed target region is generated by applying the de-blurring filter to the target region to improve sharpness of the target region. A first processed regular image comprising the first processed target region is provided.

The de-blurring filter may correspond to a deconvolution kernel.

In one embodiment, the imaging apparatus corresponds to a capsule endoscope. In another embodiment, the imaging apparatus corresponds to a traditional endoscope with a flexible tube. In yet another embodiment, the imaging apparatus corresponds to a capsule endoscope with panoramic cameras and the regular image corresponds to a panoramic image comprising multiple individual images captured by the panoramic cameras covering different fields of view.

In one embodiment, the filter determined corresponds to a Wiener filter by taking into account of a point spread function (PSF) associated with camera system and noise in the camera system.

The method may further comprise applying a second de-blurring filter to the target region of the regular image to generate a second processed regular image, where the second filter is determined based on a second target distance, and the second target distance corresponds to a small deviation from the target distance. The second processed regular image can be displayed on a display device for a user to assess visual quality of the second processed regular image. The method may further comprise applying a third de-blurring filter to the target region of the regular image to generate a third processed regular image, wherein the third filter is determined based on a third target distance, and the third target distance is modified from the second target distance in a direction depending on a user indication of visual quality comparison between the first processed regular image and the second processed regular image.

The method may further comprise receiving one or more structured-light images for a corresponding regular image, wherein said one or more structured-light images are captured using the imaging apparatus by projecting structured light onto the body lumen when the imaging apparatus is in the body lumen. The target distance is derived based on said one or more structured-light images for the corresponding regular image.

In one embodiment, the stored filter parameters are previously derived by capturing test pictures of one or more test patterns placed at various test distances in a range including a focus distance. In one embodiment, only a single test picture having a white dot at a center in black or gray background is used. In another embodiment, multiple test pictures, each having a white dot at selected location in a black or gray background, are used. In this case, said one or more filter parameters of the de-blurring filter are selected from the stored filter parameters based on the target distance and pixel location.

In one embodiment, the stored test pictures are captured using the imaging apparatus by placing one or more test patterns at various test distances from the imaging apparatus in a range including a focus distance. For example, the test patterns may correspond to a single test picture having a white dot at a center in black or gray background. In another example, the test patterns correspond to multiple test pictures, each having a white dot at selected location in a black or gray background.

A method and apparatus for characterizing an individual imaging apparatus are also disclosed. According to this method, the individual imaging apparatus is placed under a controlled environment. Test pictures for one or more test patterns are captured at multiple test distances in a range including a focus distance using the imaging apparatus, where each test picture is capture by projecting light onto a selected test pattern placed at a selected distance. The test pictures or one or more parameters of a de-blurring filter associated with the individual imaging apparatus at said multiple test distances are stored for processing images captured subsequently. The parameters of the de-blurring filter are derived from the test pictures at each test distance and the de-blurring filter corresponds to a point-spread function characterizing image formation of the individual imaging apparatus at the selected test distance.

In one embodiment, a single test picture having a white dot at a center in black or gray background is used. In another embodiment, multiple test pictures, each having a white dot at selected location in a black or gray background are used. The target point spread function corresponds to a Gaussian function. In this case, said one or more parameters may correspond to a sigma values associated with the Gaussian function.

DETAILED DESCRIPTION OF THE INVENTION

Figure 1:
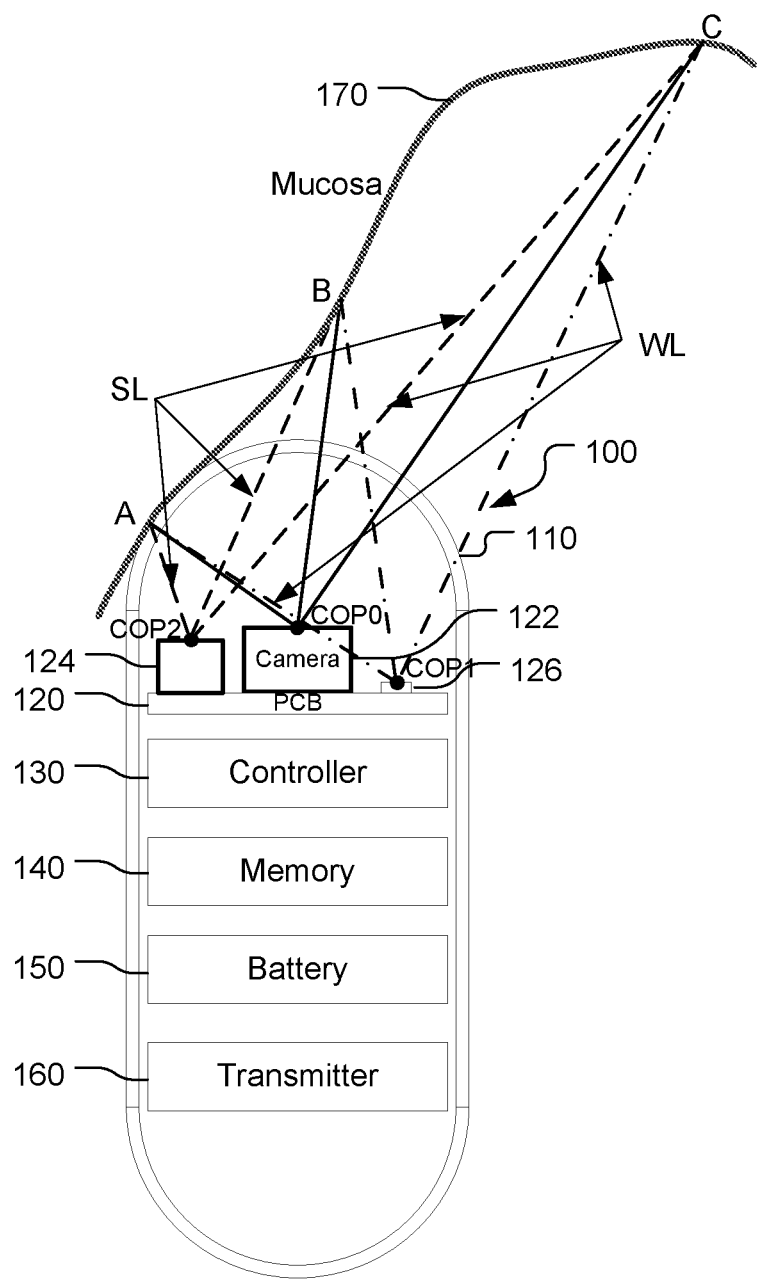
FIG. 1 illustrates an exemplary capsule endoscope with a camera and a structured-light (SL) projector for capturing regular images and SL images.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention.

Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Capsule endoscopes are used to image the mucosa of the entire gastrointestinal (GI) tract from the esophagus through the colon. Because the capsule position within the GI tract is not generally under a clinician's control, it must image both surfaces that are very close (e.g. touching the capsule) and far away (e.g., several centimeters from the capsule in larger organs such as the colon and stomach). However, the camera depth of field (DOF) is not large enough to produce an optimally sharp image over the required range of object distances. Capsule endoscope cameras are typically fixed focus. The constraints of size and power make variable focus implementation difficult, but variable focus capsule endoscopes may be deployed in the future. Nevertheless, variable focus cannot make the entire image sharp when close and far objects are in the same frame.

The DOF problem is particularly acute for capsules imaging the upper GI tract. High-resolution imaging of the esophagus has the potential to visualize cytological details including dysplasia. The esophagus is a narrow passage that mostly presses against the capsule. The close object distance results in high magnification, but good focus is still necessary to resolve details. Immediately following the esophagus is the stomach, which is a large organ, particularly when distended by gas or water to unfold its mucosa for unobstructed visualization. The neoplastic lesions that are precursors to gastric cancer can have a subtle appearance so in-focus imaging of the mucosa is required.

Magnetic fields applied from sources outside the body can be used to steer the capsule in order to visualize its entirety at proximity, but this is a laborious and time-consuming task that adds cost. Moreover, magnetic navigation is not practical in the colon, where the mucosal distance also varies from zero to several centimeters. A need exists for a capsule endoscope that can provide sharp in-focus images through the GI tract without active navigation.

Various techniques have been developed to achieve an extended the depth of field (EDOF). Most simply, the aperture of the camera can be reduced, at the expense of light-collection efficiency and a reduction of resolution from diffraction. The degree to which additional illumination energy can compensate for a reduced aperture is limited by the capacity and current-sourcing potential of batteries that fit inside a swallowable capsule.

Various digital post-processing techniques have been employed to extend the depth of field of digital images. If the point spread function (PSF) of the camera is known, it can be used to de-convolve the image to produce a sharper image, albeit with amplification of high-frequency noise. However, nulls in the PSF result in nulls in its Fourier transform (i.e., the modulation transfer function (MTF)). The spatial frequencies beyond the first MTF null cannot be recovered by deconvolution. To overcome the issue, the camera design can be adjusted to move the MTF nulls to a higher frequency. Reducing the diameter of the aperture or modulating its transparency (apodization) can move the MTF nulls out but reduce light collection. Moreover, the PSF is a function of object distance so the object distance needs to be estimated or known.

According to another post-processing technique, wavefront coding entails a phase modulation of the aperture, rather than an amplitude modulation, which results in a PSF that varies little with object distance and no reduction in light collection. A fixed deconvolution kernel can be used to sharpen the image without knowledge of object distance. Unfortunately, the large area of the PSF results in reduced SNR after deconvolution and the result is also prone to artifacts. Moreover, the phase-modulated aperture is challenging to implement consistently in a product.

Another technique for extending the DOF of a camera is presented in U.S. Pat. Nos. 7,920,172 and 8,270,083 assigned to DXO Labs, Boulogne Billancourt, France. The camera uses a lens with intentional longitudinal chromatic aberration. Blue components of an image focus at shorter object distance than red components. The high-spatial-frequency information in the blue channel is used to sharpen the green and red image components for objects close to the camera. The high-spatial-frequency information in the red channel is used to sharpen the green and blue image components for objects far from the camera. The high-spatial-frequency information in the green channel is used to sharpen the blue and red image components for objects at an intermediate distance to the camera. The method works best when the color components are highly correlated, which is mostly the case in natural environments. Moreover, human visual perception is more sensitive to variations in luminance than to chrominance, and the errors produced by the technique mostly affect chrominance. The in vivo environment is a natural one and well suited for the application this technique.

By measuring the relative sharpness of each color component in a region of the image and determining quantitative metrics of sharpness for each color, the object distance may be estimated for that region of the image. Sharpness at a pixel location can be calculated based on the local gradient in each color plane, or by other standard methods. The calculation of object distance requires knowledge of how the sharpness of each color varies with object distance, which may be determined by simulation of the lens design or by measurements with built cameras. The estimated object distance determines the filter parameters used to transfer high spatial frequency information across color channels. A challenge for this technique is accurately estimating object distance based on the relative blur in each channel. Better results are obtained if the object distance is known a priori.

A dual aperture camera is another technique to increase the DOF. The dual aperture camera reduces the aperture diameter for infrared light and utilizes an image sensor with IR sensitive pixels replacing half the green pixels. Blurred RGB channels are sharpened by information from the IR pixels. Crosstalk through the color filters from the IR to the RBG channels must be removed by a digital process. However, this cannot be done perfectly since the detailed spectrum of the sensor illumination, and hence the exact crosstalk, is not known. Some loss of resolution is also inevitable, given the replacement of some green pixels with the IR pixels.

Cameras which measure the 4-dimensional light field are perhaps the most effective at achieving refocusing in post processing. The most compact of these is the plenoptic camera, which unfortunately requires many extra pixels as well as many micro lens to achieve the desired resolution and is hence not suitable for very small cameras as required for endoscopes.

Whether defocus is corrected by transferring information across color channels or by deconvolution or other algorithms, the process is simpler and less prone to error and artifacts if a separate sensor measures a depth map which is provided to the EDOF algorithm. A structured light projector can be combined with a camera to provide depth information by triangulation. An endoscope with a structure light projector is presented in a co-pending U.S. patent application Ser. No. 15/927,856, filed on Mar. 21, 2018 and published as US 2018/0213207 on Jul. 26, 2018, which is assigned to the same assignee as the present application. The U.S. patent application Ser. No. 15/927,856 claims priority to U.S. patent application Ser. No. 14/884,788, filed on Oct. 16, 2015, now U.S. Pat. No. 9,936,151.

According to the invention disclosed in U.S. Pat. No. 9,936,151, structured-light images and regular images are captured separately. Depth information associated with the image contents are derived from the structured-light images. The depth information derived can be used by the corresponding regular images to establish a 3-D model of the contents. Various ways to capture mixed structured-light images and regular images have been disclosed in U.S. Pat. No. 9,936,151.

The depth map from SL can be used to determine a de-convolution kernel for each portion of the image. Since the SL may not produce a depth map with pixel-level resolution, the algorithm may refine the depth map by image-analysis algorithms such as depth-from-shading (or shape from shading) and edge detection.

FIG. 1 illustrates an exemplary capsule endoscope with a camera 122 and an SL projector 124. Components of the SL projector and the camera may be mounted on one or more printed circuit boards (PCBs) 120. The capsule endoscope 100 includes at least one white light (WL) illuminator 126, which may comprise a blue LED and a phosphor, a controller 130 for controlling the endoscope system and processing data, a memory 140 for storing images captured by the camera, a battery 150 for powering the capsule, and an optional transmitter 160 for transmitting image data from the capsule. If non-volatile memory with sufficient capacity is used to store the captured images, the optional transmitter 160 may not be needed. The components mentioned above are enclosed in a water-sealed housing. Furthermore, the shape of capsule housing is adapted for easy swallowing by a human subject through the mouth. The image data includes images captured of the GI tract mucosa with the white light illumination and with the SL projector illuminating the mucosa 170.

Some frames may use WL illumination, some SL, and some both. The SL projector shines SL onto point A, touching the capsule, point B, at an intermediate distance, and point C, at a greater distance. The camera captures an image that includes points A, B, and C. The centers of perspective of the camera and SL projector, COP0 and COP2, are not collocated so the positions of the points A, B, and C in 3D space can be estimated by triangulation based on the position in the image of spatial features such as spots in the projected SL located at points A, B, and C. The term COP refers to center of perspective. The estimation typically relies on calibration data for the camera and SL projector. Many well-known techniques for processing images of projected SL can be applied to determine a depth map for images of objects captured by the apparatus. These depth maps may also be applied to other frames that do not include SL captured at times close to, but not coincident with, one or more SL frames. Various interpolation and motion estimation algorithms may be applied to account for the small movement of objects in the WL frames relative to the SL frames.

The difference in object distance from the camera for point A and point C may not be within the DOF of the camera so that one or the other or both is not sufficiently focused. The focus of the camera may be optimized for objects at an intermediate distance, such as point B, and both point A and point C may be blurry in the captured image. The SL image data allows for the computation of a depth map for WL image data, which in turn allows for the calculation of a PSF map of the WL image data, utilizing the depth map and a model of the camera. An SL image and a corresponding WL image have to be captured very close in time so that the camera movement is relatively small. Otherwise, the derived depth map may be very different from the true depth map of the WL image. The model of camera may include parameters such as the focal length, f/# (f being the focal length and # being the aperture diameter), distortion, and lens aberrations. Furthermore, the model of the camera may also include camera calibration data. From the PSF map, the image may be sharpened by deconvolution with kernels derived from the PSF.

The kernel for deconvolution generally varies across the image as a function of depth. Let the kernel be a function $h(\cdot)$, where the kernel is distance- or depth-dependent (i.e., $h(d)$). Furthermore, the depth map may have different values at different locations. In other words, the depth is location dependent (i.e., $d(x,y)$). Accordingly, the kernel is represent by $h(d(x,y))$.

Figure 2:
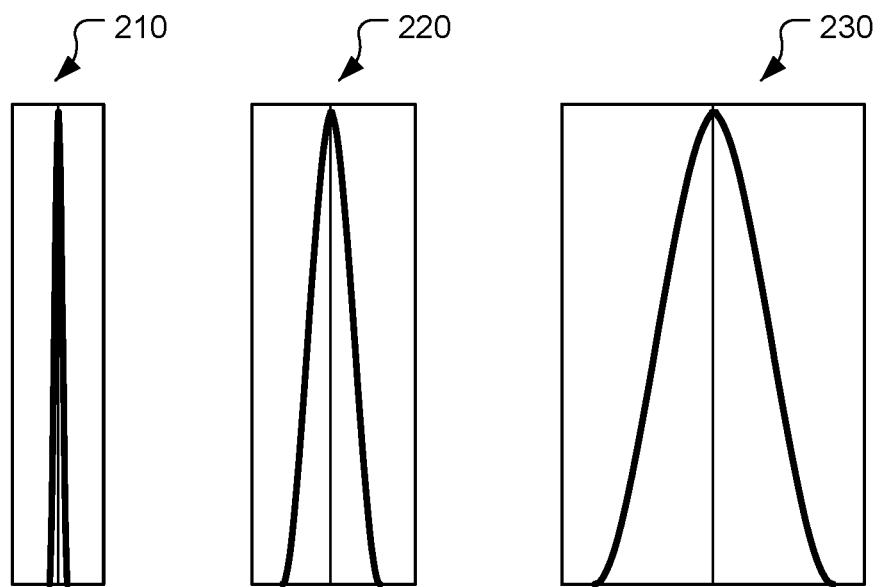
FIG. 2 illustrates some examples of convolution kernel corresponding to point spread function (PSF) of a camera system.

FIG. 2 illustrates some examples of convolution kernel. Curve 210 corresponds to the point spread function of a well-focused case, where the image corresponding to a point source appears as a small dot. Curve 220 corresponds to the point spread function of a slight-defocused case, where the image corresponding to a point source appears as a slightly larger dot. Curve 230 corresponds to the point spread function of a defocused case, where the image corresponding to a point source appears as a much larger dot.

The image formation for an source object s can be described as follows:

$$r = s*h + n. \quad (1)$$

In the above equation, r corresponds to the image captured, h corresponds to the point spread function, n corresponds to the noise and "*" corresponds to the convolution operation. The corresponding operation in the frequency domain can be represented as:

$$R = S \cdot H + N. \quad (2)$$

Figure 3A:
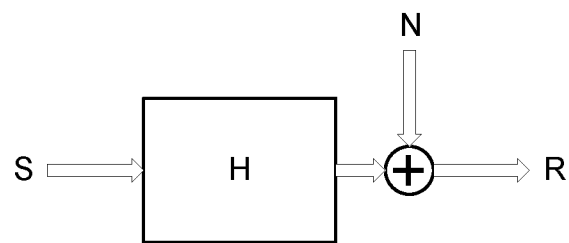
FIG. 3A illustrates an exemplary image formation model with additive noise for a camera system.
Figure 3B:
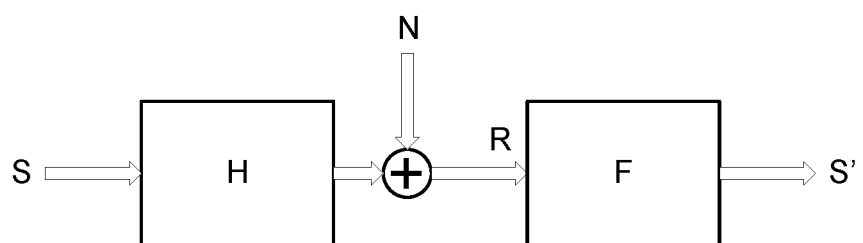
FIG. 3B illustrates an exemplary de-blurring model in frequency domain for sharpening a blurred image.

In the above equation, R, H, S and N correspond to the Fourier Transforms of r, h, s and n respectively and "·" corresponds to the point-wise multiplication operation. An exemplary image formation model with additive noise is shown in FIG. 3A. The image R formed according to this model may contain blurred regions due to out of focus. In order to sharpen the blurred images, de-blurring can be applied to the formed image R. An exemplary de-blurring model in frequency domain is shown in FIG. 3B, where F corresponds to Fourier Transform of the de-blurring filter. Accordingly, the sharpened image S' is derived according to:

$$S' = F \cdot R = F \cdot (S \cdot H + N).$$

If there is no noise (i.e., n=0), the Fourier Transform F of the de-blurring filter is derived as:

$$F = H^{-1}.$$

In the above equation, $H^{-1}$ corresponds to the inverse function of H. In this case, $S' = H^{-1} \cdot (S \cdot H + N)$.

In the case with an additive noise, the de-blurring filter can be designed to minimize the mean-square error between the sharpened image and the original image. For a Gaussian noise model, the de-blurring filter becomes a Wiener Filter, F:

$$F = \frac{H^*|S|}{|H|^2|S| + |N|}.$$

In the above equation, H* corresponds to the conjugate of H. The frequency domain filter F can be transformed back to a corresponding spatial domain filter f, which can be convolved with the formed image r to generate a sharpened image s', i.e., s'=r*f. In other words, a deconvolution kernel, f can be applied to the captured image r, which may contain blurred regions due to out of focus and noise. The deconvolution kernel, f is depth dependent. The depth in turn is dependent on image location. Accordingly, the deconvolution kernel, f can be represented as f(d(x,y)). The filter is specified by the filter parameters, such as the type of mathematical function (e.g. a rational function) and coefficients. If a fixed deconvolution kernel is applied to a smaller region, the deconvolution kernel, f can be represented as f(d(i)), for region i. Other deconvolution algorithms, such as Lucy-Richardson, may be employed instead of Wiener deconvolution.

Algorithms other than deconvolution, such as maximum-likelihood estimation may be employed to sharpen the image based on the depth map. Moreover, the PSF may not need to be calculated as an intermediate step. Sharpening of one or more color planes of the image may be accomplished for each region of the image by transferring high-spatial-frequency information from a color plane that is sharper in the image region to one or more color planes that are less sharp in that region employing digital filter parameters determined by the depth map.

Figure 4:
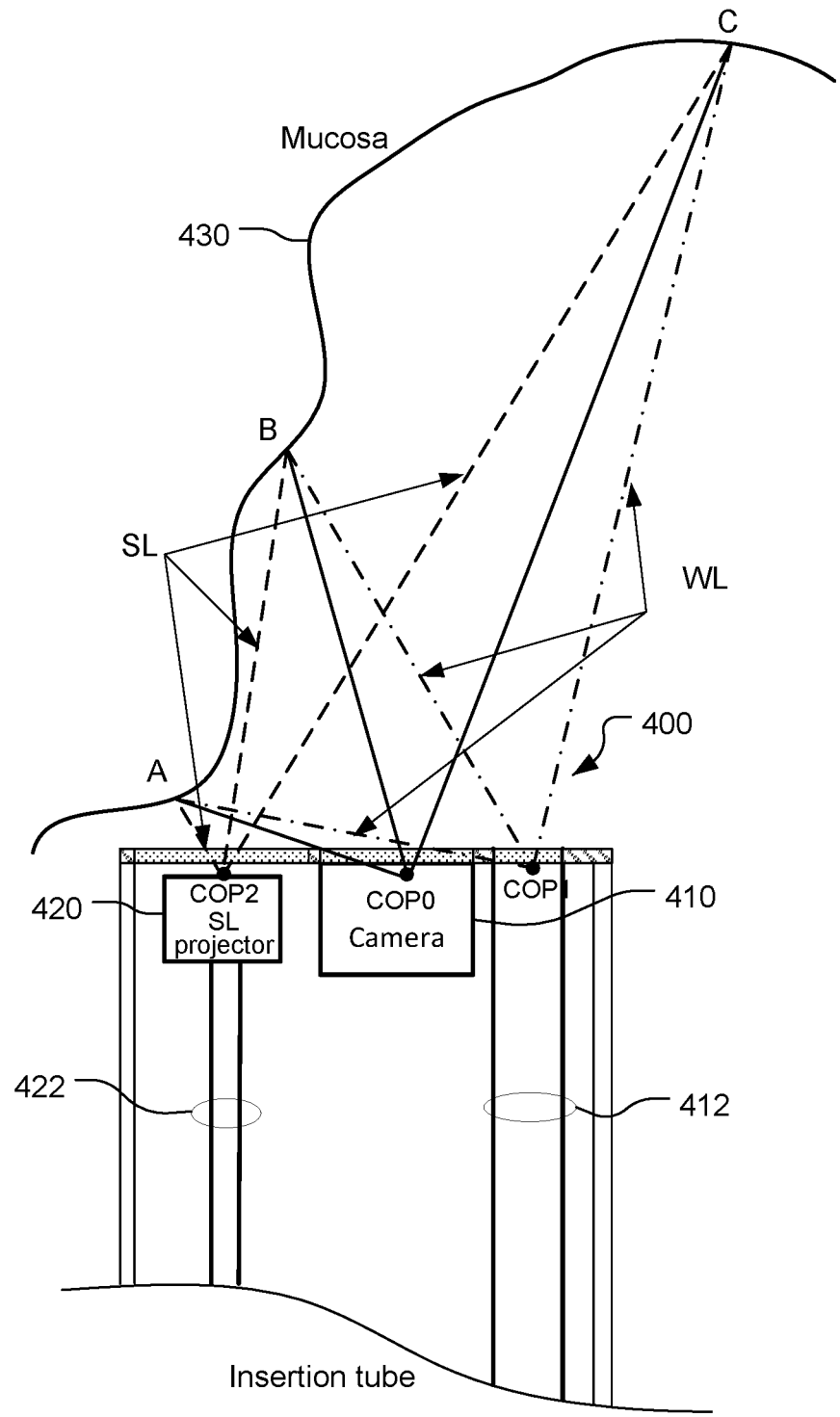
FIG. 4 shows an imaging device for capturing regular images and SL images based on the type of traditional endoscope with a flexible tube for inserting the camera.

FIG. 4 shows a similar situation with the type of traditional endoscope with a flexible tube for inserting the camera. The camera 410 and the SL projector 420 are at or near the tip of an insertion tube 400, which enters the patient's body through an orifice or incision. The WL source and the SL light source may be external to the patient and carried up the insertion tube in channels (WL source/channel 412 and SL source/channel 422) such as light guides or optical fibers. Either the SL light source, the WL light source, or both may also be located near the tip of the endoscope in the body. The SL projector shines SL onto point A, at a very close distance, point B, at an intermediate distance, and point C, at a greater distance. The camera captures an image that includes points A, B, and C. The centers of perspective of the camera and SL projector, COP0 and COP2, are not collocated so the positions of the points A, B, and C in 3D space can be estimated by triangulation based on the position in the image of spatial features such as spots in the projected SL located at points A, B, and C.

Figure 5:
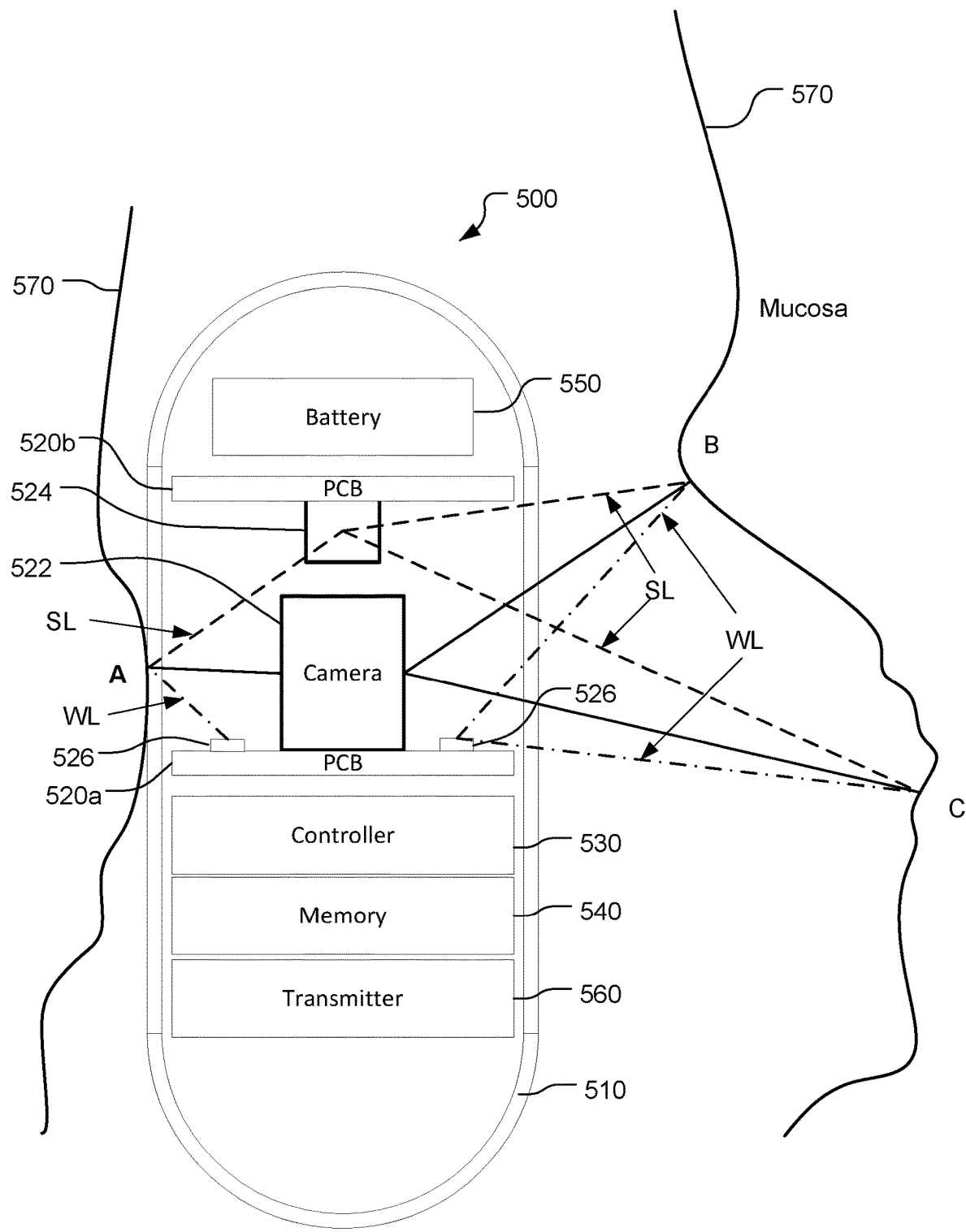
FIG. 5 shows an exemplary capsule endoscope with a panoramic camera and a structured-light (SL) projector for capturing panoramic regular images and SL images.

FIG. 5 shows a capsule endoscope 500 with one or more cameras 522 that image through tubular side walls of the capsule rather than one or more of the endcaps. When multiple cameras are used, the cameras are arranged to cover different fields of view in order to capture panoramic images. The WL sources 526, such as LEDs, and one or more SL projectors 524 illuminate mucosa 570 located transverse to the capsule. The one or more cameras 522 may capture a 360 degree panoramic image of the mucosa, and the WL 526 and SL sources (inside the SL projector 524) may illuminate over the same 360 degree panorama. Each camera and SL projector are not collocated, allowing a depth map to be determined for objects imaged by the cameras. FIG. 5 also shows that components of the SL projector and the camera may be mounted on one or more printed circuit boards (PCBs) 520*a* and 520*b*. The capsule endoscope 500 also includes a controller 530 for controlling the endoscope system and processing data, a memory 540 for storing images captured by the camera, a battery 550 for powering the capsule, and a transmitter 560 for transmitting image data from the capsule. The components mentioned above are enclosed in a water-sealed housing 510.

The image processing may be performed by the controller inside the capsule. It may also be performed on the data outside the capsule after it has been transmitted by the transmitter. The image processing can also be performed partially by the controller inside the capsule and partially by the external processor or systems such as a workstation, viewing station, computer or laptop.

In one embodiment, for a target regular image, the depth information or depth map associated with the target regular image is derived from one or more corresponding structured-light images. Based on the depth map and camera parameters, a suitable deconvolution kernel can be determined for each region. The region is preferred to be small enough so that a fixed kernel is expected to work well to sharpen the small region. The small region can be as small as one pixel. The sharpening processing can be performed on-the-fly when the capsule image sequence is viewed. Alternatively, the sharpening process can be performed offline, or pre-processed and stored. The sharpened image sequence can be retrieved and viewed by a clinician. The sharpened image sequence may be stored along with the original image sequence. The clinician may be provided the option to display original images, the sharpened images or both.

In another embodiment, rather than processing the entire video prior to viewing by a clinician, each frame may be processed on the fly as the video is reviewed. The video reader (user of a computer or similar system with a video display and a user interface) may pause the video and examine one or more particular frames, which may be captured for inclusion in a report or database associated with the medical procedure. These frames may be sharpened after they are designated by the reader through the user interface (UI). Rather than using depth information to determine the parameters for image sharpening, the system may progressively apply processing to a frame corresponding to a progression of assumed object distances. The apparent affect is as if the camera were progressively refocused for different object distances, from near to far or far to near. This refocusing may be accomplished automatically or under the control of the user (reader). The user can optimize the refocusing (sharpening) for one or more regions of interest (ROIs) that have clinical significance, such as suspected lesions on the mucosa. On the other hand, after sharpening the images according to the respective different distances corresponding to different areas in the field of view, a 2D or 3D images could be constructed by putting these images together so that reading the image becomes instantaneous.

The depth information derived may not be accurate due to various reasons such as noise and low SL image resolution, as well as the time difference between SL and WL images are captured. Therefore, in yet another embodiment, a regular image can be initially sharpened according to the depth information derived from one or more corresponding structured-light images. After the initial sharpening, the regular image can be refocused using a deconvolution kernel corresponding to a distance slightly deviated from the depth map derived for the target region from the structured-light images. For example, a step size equal to $\Delta$ can be added to or subtracted from the distance derived from the SL image. The clinician can provide feedback to indicate whether the visual quality is better or worse. According to the indication, the system may apply further refocusing. For example, if the quality is improving when $\Delta$ is added to the original distance, the $\Delta$ or a smaller step size can be further added to the modified distance. Or, if the quality is improving when $\Delta$ is subtracted from the original distance, the $\Delta$ or a smaller step size can be further subtracted from the modified distance.

3D information about the GI tract derived from the SL image data can be used to modify parameters of the endoscope camera. If a camera in the endoscope includes adjustable focus, the depth information from SL may be used to focus the camera, for example by changing the back focus distance of the camera, the spacing of lens elements in the lens module of the camera, or modulating the focal length of a lens element in the camera such as a "liquid" lens.

Furthermore, the resolution of the image sensor of the camera (e.g. CMOS or CCD image sensor) may be adjusted globally or over one or more regions of interest (ROIs) based on depth information derived from SL. The size and location of the ROIs may also be so derived. The image may also be cropped around the ROIs. These techniques allow for the storage of increased resolution images of in vivo surfaces that are of potential clinical significance or that require increased sensor resolution to compensate for large object distance, while conserving system resources such as battery energy and archival memory by reducing the resolution of and/or cropping image regions of lesser clinical importance or requiring lesser sensor resolution for adequate visualization and clinical evaluation. Sensor resolution can be reduced by binning signals from multiple pixels together or by subsampling pixel signals. Resolution can also be reduced after reading the data from the pixels by binning, low pass filtering, and image compression.

When using a capsule endoscope to image the stomach, the full resolution of the sensor may be needed to adequately image tissues that are distant from the endoscope and therefor at lower magnification, while tissues (mucosal surfaces) close to the endoscope may not require the full sensor resolution. Based on the SL-derived depth map, ROIs or complete image frames can be delineated for selective resolution adjustment and/or cropping. If cytological imaging in the esophagus is required, then full resolution may be employed when a close object distance is detected early in the video. Once large object distances are detected, corresponding to the capsule entering the stomach, the resolution of the image sensor could be reduced. Generally, SL-derived depth information can used to estimate when the capsule transitions from one portion of the GI tract to another, where there is a size difference between the portions, and modify parameters of the capsule endoscope including camera focus, resolution, ROI number and location, cropping, exposure, illumination levels, frame rate, image compression parameters (e.g. quantization), motion estimation parameters (which may determine how frames are processed based on estimated motion or image change from one frame to another), and image processing algorithms and parameters.

The present invention can be implemented in various forms. For example, it can be implemented based on a computer with a display device such a workstation with a display, a desktop with a display or a laptop. When a laptop is used, the regular images and structured images from a capsule camera or an endoscope can be downloaded into the computer storage or can be accessed remotely through networks or clouds. The CPU in the laptop can be used to derive the depth map based on the structured-light image. Accordingly, the de-convolution kernel for each target region of the regular image can be determined according to the distance of the target region and camera parameters. The deconvolution operations can be performed by the laptop CPU. The processed image along with other information can be displayed on the laptop screen. When a user interface (UI), such as indicating visual quality judgement, is needed, the key board or a computer mouse can be used.

In the above disclosure, the filter parameters have to be derived based on the target distance and camera parameters associated with the imaging apparatus. According to another embodiment of the present invention, the point spread function at various depths are measured and stored. For example, a picture with a white dot in middle of black ground can be used as the test image. The test picture is placed in the focus distance and various distances in front of and behind the focus distances. Pictures at these distances are taken for determining parameter(s) of the point spread functions at corresponding distances. With known parameter (s) of the point spread functions at corresponding distances, the corresponding deconvolution filters can be determined (e.g. based on Wiener filter design). Therefore, parameters of the deconvolution filters can be determined with known parameter(s) of the point spread functions at corresponding distances. For a capture regular image, the distance information can be derived from corresponding structured light image(s). Accordingly, a deconvolution filter can be selected for each pixel location based on the distance.

While the derived filter parameters can be stored for each individual imaging apparatus, the captured test pictures can also be stored. When the de-blurring operations are performed, the filter parameters can be derived based on the test pictures associated with a selected test distance. With the increasing processing power in a viewing station or a laptop computer, the filter parameter derivation can be derived on the fly.

In one embodiment, the point spread function is circular (i.e., the same point spread function dependent on the radial distance from the origin) and furthermore, the point spread function is approximated as a Gaussian function:

$$h(r) = \frac{1}{\sigma\sqrt{2}} e^{-r^2/2\sigma^2}.$$

For the Gaussian function, we need to determine the parameter, $\sigma$ for various distances around depth of focus $D_0$. In one embodiment, the $\sigma$ value is determined based on the radius, r of the captured test picture. The radius can be defined as the radial distance that the maximum intensity at the center drops to a pre-defined level (relative to the maximum intensity). For example, the pre-defined can be 0.6065 (i.e., $e^{-1/2}$). In this case, the radius, r is equal to the $\sigma$ value. If the pre-defined level is 0.5, the $\sigma$ value is equal to 0.8493*r. The $\sigma$ values for various distances can be stored. For example, the $\sigma$ values for various distances can be stored in a lookup table. As mentioned before, the deconvolution kernel can be determined based on the filter parameter and a noise model according to Wiener filter design or other algorithms.

In the above embodiment, we have assumed that the point spread function is only dependent on the distance of a select pixel and is independent of the pixel location. However, this model may not be accurate if sensor plane or camera lens are non-uniform or asymmetric. For a more flexible model, the point spread function is measured at different locations for various distances. For example, the point spread function can be measured at a set of pre-defined locations. In practice, the point spread function may not be measured at every pixel location. If the point spread function is not measured at a selected location, the point spread function at the selected location can be derived from neighboring locations having measured point spread function for a given distance.

In yet another embodiment, a test picture having multiple white dots in black or gray background at pre-determined locations can be used for determining the point spread function at these locations.

While a test picture with a single or multiple point sources are used, other test patterns may also be used. For example, instead of white dot on a black background, the test picture may have reverse intensities (i.e., a black dot in a white background).

Figure 6:
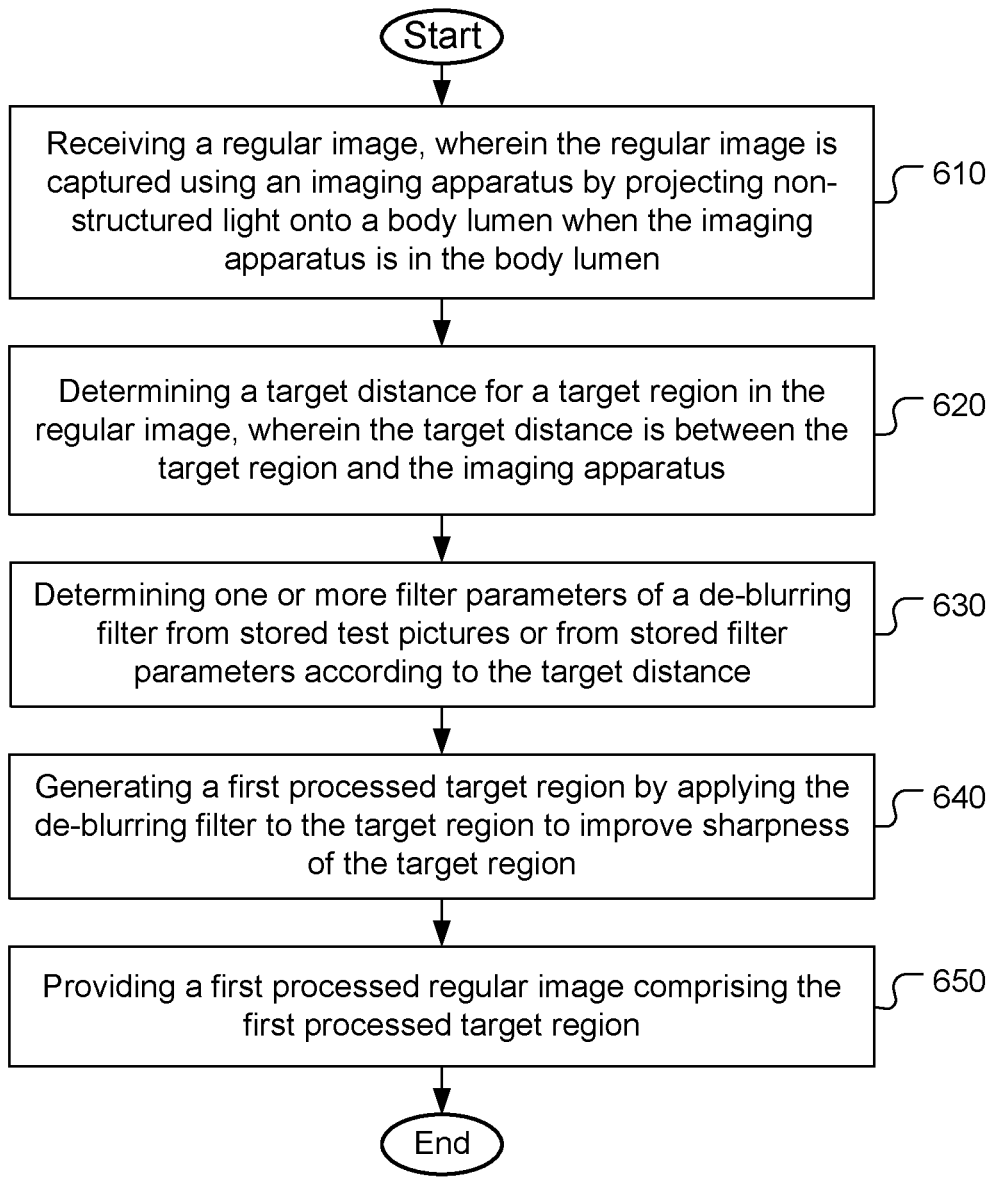
FIG. 6 illustrates an exemplary flowchart for system incorporating an embodiment of the present invention to sharpen regular images utilizing distance information derived from one or more corresponding structured-light images.

FIG. 6 illustrates an exemplary flowchart for system incorporating an embodiment of the present invention to sharpen regular images utilizing distance information derived from one or more structured-light images. The steps shown in the flowchart may be implemented as program codes executable on one or more processors (e.g., one or more CPUs). According to this method, a regular image is received in step 610, wherein the regular image is captured using an imaging apparatus by projecting non-structured light onto a body lumen when the imaging apparatus is in the body lumen. A target distance for a target region in the regular image is determined in step 620, wherein the target distance is between the target region and the imaging apparatus. One or more filter parameters of a de-blurring filter are determined from stored test pictures or from stored filter parameters according to the target distance in step 630. A first processed target region is generated by applying the de-blurring filter to the target region to improve sharpness of the target region in step 640. A first processed regular image comprising the first processed target region is provided in step 650.

Figure 7:
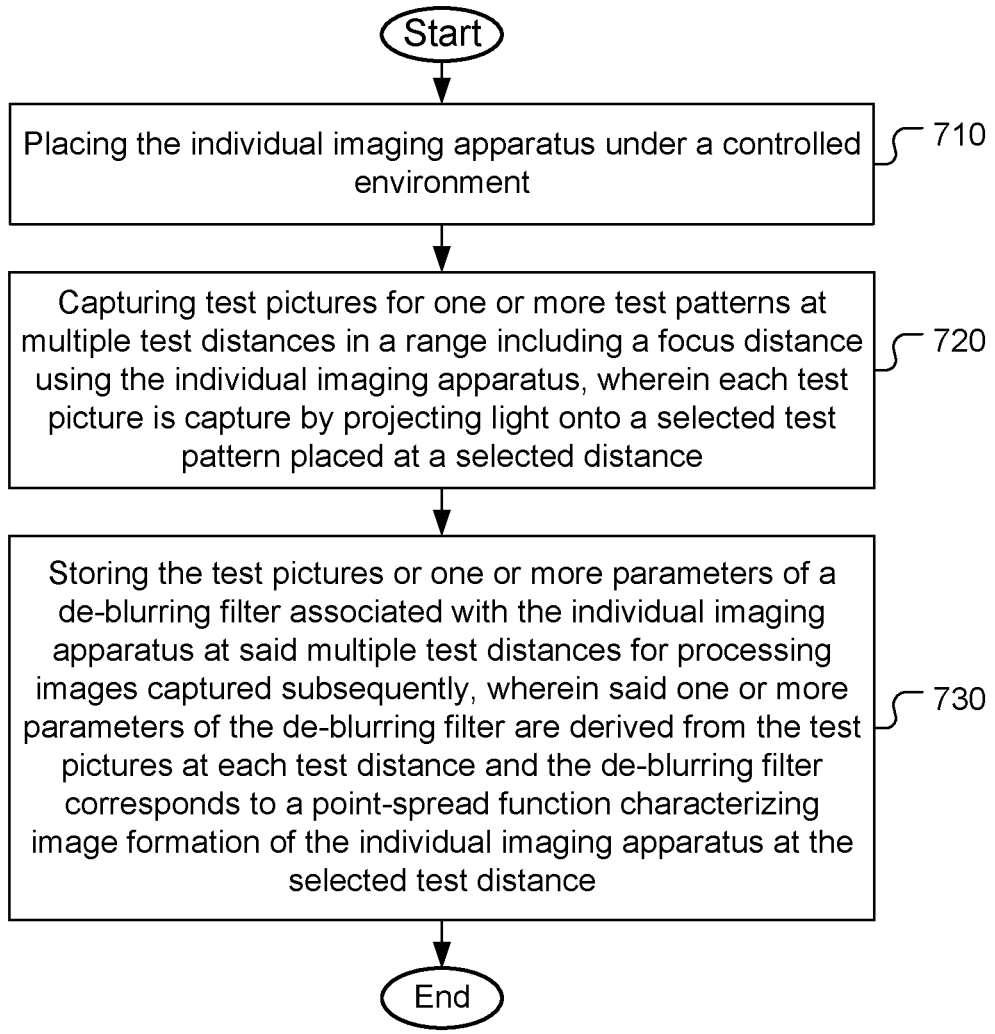
FIG. 7 illustrates an exemplary flowchart for characterizing an imaging apparatus incorporating an embodiment of the present invention.

FIG. 7 illustrates an exemplary flowchart for characterizing an imaging apparatus incorporating an embodiment of the present invention. According to this method, the individual imaging apparatus is placed under a controlled environment in step 710. For example, the controlled environment may correspond to a set up without ambient light. Test pictures for one or more test patterns are captured at multiple test distances in a range including a focus distance using the individual imaging apparatus in step 720, wherein each test picture is capture by projecting light onto a selected test pattern placed at a selected distance. The test pictures or one or more parameters of a de-blurring filter associated with the individual imaging apparatus at said multiple test distances are stored for processing images captured subsequently in step 730, wherein said one or more parameters of the de-blurring filter are derived from the test pictures at each test distance and the de-blurring filter corresponds to a point-spread function characterizing image formation of the individual imaging apparatus at the selected test distance.

The flowcharts shown are intended to illustrate examples of object distance/size estimation using camera calibration data according to the present invention. A person skilled in the art may modify each step, re-arranges the steps, split a step, or combine steps to practice the present invention without departing from the spirit of the present invention.

Due to variations during manufacturing or other reasons, the characteristics of each imaging apparatus may not be the same. Therefore, the process to characterize the imaging apparatus has to be done individually. The derived characteristics such as the point spread functions have to be stored for individual imaging apparatus. During imaging sharpening for images captured by a target imaging apparatus, the stored characteristics (i.e., the point spread function parameters or the filter parameters) for the target imaging apparatus need to be retrieved and applied.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method for processing gastrointestinal (GI) images, comprising:
   receiving a regular image, wherein the regular image is captured using an imaging apparatus by projecting non-structured light onto a body lumen when the imaging apparatus is in the body lumen;
   determining a target distance for a target region in the regular image, wherein the target distance is between the target region and the imaging apparatus;
   determining one or more filter parameters of a de-blurring filter from stored test pictures or from stored filter parameters according to the target distance;
   generating a first processed target region by applying the de-blurring filter to the target region to improve sharpness of the target region; and
   providing a first processed regular image comprising the first processed target region.

2. The method of claim 1, wherein the de-blurring filter corresponds to a deconvolution kernel.

3. The method of claim 1, wherein the imaging apparatus corresponds to a capsule endoscope.

4. The method of claim 1, wherein the imaging apparatus corresponds to a traditional endoscope with a flexible tube.

5. The method of claim 1, wherein the imaging apparatus corresponds to a capsule endoscope with panoramic cameras and the regular image corresponds to a panoramic image comprising multiple individual images captured by the panoramic cameras covering different fields of view.

6. The method of claim 1, wherein the de-blurring filter corresponds to a Wiener filter by taking into account of a point spread function (PSF) associated with camera system and noise in the camera system.

7. The method of claim 1, further comprising:
   applying a second de-blurring filter to the target region of the regular image to generate a second processed regular image, wherein the second de-blurring filter corresponds to a second target distance with a small deviation from the target distance.

8. The method of claim 7, further comprising displaying the second processed regular image on a display device for a user to assess visual quality of the second processed regular image.

9. The method of claim 8, further comprising:
   applying a third de-blurring filter to the target region of the regular image to generate a third processed regular image, wherein the third de-blurring filter corresponds to a third target distance modified from the second target distance in a direction depending on a user indication of visual quality comparison between the first processed regular image and the second processed regular image.

10. The method of claim 1, further comprising receiving one or more structured-light images for a corresponding regular image, wherein said one or more structured-light images are captured using the imaging apparatus by projecting structured light onto the body lumen when the imaging apparatus is in the body lumen.

11. The method of claim 10, the target distance is derived based on said one or more structured-light images for the corresponding regular image.

12. The method of claim 1, wherein the stored filter parameters are previously derived by capturing test pictures of one or more test patterns placed at various test distances in a range.

13. The method of claim 12, wherein the test pictures of one or more test patterns correspond to a single test picture having a white dot at a center in black or gray background.

14. The method of claim 12, wherein the test pictures of one or more test patterns correspond to multiple test pictures, each having a white dot at selected location in a black or gray background.

15. The method of claim 14, wherein said one or more filter parameters of the de-blurring filter are selected from the stored filter parameters based on the target distance and pixel location.

16. The method of claim 12, wherein the range includes a focus distance.

17. The method of claim 1, wherein the stored filter parameters are previously derived for an individual imaging apparatus by capturing test pictures of one or more test patterns placed at various test distances from the individual imaging apparatus.

18. The method of claim 1, wherein the stored test pictures are captured using the imaging apparatus by placing one or more test patterns at various test distances from the imaging apparatus in a range.

19. The method of claim 18, wherein said one or more test patterns correspond to a single test picture having a white dot at a center in black or gray background.

20. The method of claim 18, wherein said one or more test patterns correspond to multiple test pictures, each having a white dot at selected location in a black or gray background.

21. The method of claim 18, wherein the range includes a focus distance.

22. An apparatus for processing gastrointestinal (GI) images, comprising a processor configured to:
   receive a regular image, wherein the regular image is captured using an imaging apparatus by projecting non-structured light onto a body lumen when the imaging apparatus is in the body lumen;
   determine a target distance for a target region in the regular image, wherein the target distance is between the target region and the imaging apparatus;
   determine one or more filter parameters of a de-blurring filter from stored test pictures or from stored filter parameters according to the target distance;
   generate a first processed target region by applying the de-blurring filter to the target region to improve sharpness of the target region; and
   provide a first processed regular image comprising the first processed target region.

23. The apparatus of claim 22, wherein the stored filter parameters are previously derived for an individual imaging apparatus by capturing test pictures of one or more test patterns placed at various test distances from the individual imaging apparatus.

24. A method for characterizing an individual imaging apparatus, comprising:
placing the individual imaging apparatus under a controlled environment;
capturing test pictures for one or more test patterns at multiple test distances in a range including a focus distance using the individual imaging apparatus, wherein each test picture is capture by projecting light onto a selected test pattern placed at a selected test distance; and
storing the test pictures or one or more parameters of a de-blurring filter associated with the individual imaging apparatus at said multiple test distances for processing images captured subsequently, wherein said one or more parameters of the de-blurring filter are derived from the test pictures at each test distance and the de-blurring filter corresponds to a point-spread function characterizing image formation of the individual imaging apparatus at the selected test distance.

25. The method of claim 24, wherein said one or more test patterns correspond to a single test picture having a white dot at a center in black or gray background.

26. The method of claim 24, wherein said one or more test patterns correspond to a single test picture having multiple white dots in black or gray background at pre-determined locations.

27. The method of claim 24, wherein said one or more test patterns correspond to multiple test pictures, each having a white dot at selected location in a black or gray background.

28. The method of claim 24, wherein the point-spread function corresponds to a Gaussian function.

29. The method of claim 28, wherein said one or more test patterns correspond to multiple test pictures, each having a white dot at selected location in a black or gray background, and said one or more parameters correspond to a sigma value associated with the Gaussian function.

30. An apparatus for characterizing an individual imaging apparatus, comprising a processor configured to:
place the individual imaging apparatus under a controlled environment;
capture test pictures for one or more test patterns at multiple test distances in a range including a focus distance using the individual imaging apparatus, wherein each test picture is capture by projecting light onto a selected test pattern placed at a selected test distance; and
store the test pictures or one or more parameters of a de-blurring filter associated with the individual imaging apparatus at said multiple test distances for processing images captured subsequently, wherein said one or more parameters of the de-blurring filter are derived from the test pictures at each test distance and the de-blurring filter corresponds to a point-spread function characterizing image formation of the individual imaging apparatus at the selected test distance.

* * * * *